United States Patent [19]  [11] 4,046,800
Hessler  [45] Sept. 6, 1977

[54] CIS-β-[TRIMETHYLAMMONIUM]-ACRYLONITRILE TOSYLATE

[75] Inventor: Edward J. Hessler, Kalamazoo, Mich.

[73] Assignee: The Upjohn Company, Kalamazoo, Mich.

[21] Appl. No.: 692,947

[22] Filed: June 4, 1976

Related U.S. Application Data

[62] Division of Ser. No. 546,074, Jan. 31, 1975, Pat. No. 3,978,042.

[51] Int. Cl.$^2$ ........................................... C07C 121/78
[52] U.S. Cl. ................................................. 260/465 E
[58] Field of Search ...................... 260/456 A, 465 E

[56] References Cited

PUBLICATIONS

Gundermann et al. Chemical Abstracts, vol. 71, 101497p (1969).

*Primary Examiner*—Dolph H. Torrence
*Attorney, Agent, or Firm*—Martin B. Barancik

[57] ABSTRACT

A new method for preparing cytosine arabinoside involving the cyanovinylation of the aminooxazoline of D-arabinose by cis-β-[trimethylammonium]-acrylonitrile tosylate. Also included are new preparations of the aminooxazoline of D-arabinose and the anion of cis-1-cyano-2-hydroxyethylene.

1 Claim, No Drawings

# CIS-β-[TRIMETHYLAMMONIUM]-ACRYLONITRILE TOSYLATE

CROSS REFERENCE TO RELATED APPLICATIONS

This is a divisional application of copending application Ser. No. 546,074, filed Jan. 31, 1975 now issued as U.S. Pat. No. 3,978,042.

DESCRIPTION OF THE PRIOR ART

Cytosine arabinoside, also known as 1-β-D-arabinofuranosylcytosine, is a known anti-leukemic agent. Consequently, an economical and safe synthesis of the compound and other significant cytosine nucleosides is an important contribution to the well being of the populace. The Orgel and Sanchez patent, U.S. Pat. No. 3,658,788, provided a new way of preparing cytosine nucleosides, particularly cytosine arabinoside. The process consisted of preparing an aminooxazoline intermediate which is then cyanovinylated to a cyclocytidine salt. The cyclocitidine salt is then treated with aqueous ammonia to form the cytosine nucleoside. However, difficulties accompany these synthetic pathways. In the cyanovinylation step, many of the electrophilic reagents were too costly to use in a commercially oriented process. Those reagents that were commercially feasible, cost-wise, suffered from other serious defects. Cyanoacetylene, for example, is extremely hazardous because of its tendency to explode.

A new process for preparing cytosine arabinoside has been discovered. Although the synthesis goes through the aminooxazoline intermediate, a separate isolation step of this intermediate is not required. Furthermore, a new cyanovinylating agent without the serious problems of the past agents has now been discovered. The invention also includes new methods for preparing the aminooxazoline and the cyanovinylating agent.

BRIEF SUMMARY OF THE INVENTION

A process for preparing cyclocytidine tosylate salt has been discovered which comprises:

a. reacting D-arabinose with cyanamide or cyanide plus aqueous ammonia in an inert solvent to prepare the aminooxazoline of D-arabinose b. contacting the said aminooxazoline of Step a with cis-β-[trimethylammonium]-acrylonitrile tosylate.

A further aspect of the invention is the preparation of the aminooxazoline of D-arabinose which comprises reacting D-arabinose with cyanamide in an inert, aprotic solvent in an essentially dry environment with catalytic quantities of a base present.

A still further aspect of this invention is the preparation of the compound

FIG. 1

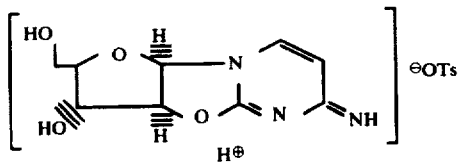

which comprises reacting the aminooxazoline of D-arabinose with cis-β-[trimethylammonium]-acrylonitrile tosylate.

Another aspect of this invention is the selective preparation of the anion of cis-1-cyano-2-hydroxyethylene which comprises contacting isoxazole with a base of a strength equal to or greater than sodium methoxide which is an inert organic solvent at a temperature less than or equal to −40° C. It has also been found that the temperature of the isoxazole at the time of the addition is critical. If isoxazole is at an ambient temperature, the −40° C. is essential for proper yields of the cis anion. However, if the isozazole is cooled prior to addition, the reaction solution may be maintained at a higher temperature.

A further aspect of the invention is the compound cis-β-[trimethylammonium]-acrylonitrile tosylate.

DETAILED DESCRIPTION OF THE INVENTION

A similar pathway to cytosine arabinoside, through the aminooxazoline intermediate, is illustrated in the aforementioned Orgel and Sanchez patent. With regard to preparing the aminooxazoline of cytosine arabinoside, the disclosure of Orgel and Sanchez appearing at Column 4, line 63 to Column 6, line 11, is herein incorporated by reference. A new, more preferred method of preparing the aminooxazoline has been discovered. This method comprises reacting D-arabinose with cyanamide in an inert, aprotic solvent in an essentially dry environment with catalytic quantities of a base present to form the aminooxazoline of D-arabinose. Rather than working in an aqueous system, an essentially dry system is preferred. Consequently, cyanamide is preferred over the usually aqueous system of ammonia and cyanogen. Cyanamide can be obtained commercially as solid calcium cyanamide or as an aqueous solution of cyanamide. However, the calcium cyanamide can be converted to free cyanamide by the addition of hydrochloric acid followed by extractive purification. Anhydrous cyanamide can be additionally prepared by contacting aqueous cyanamide with calcium chloride followed by ethyl acetate extraction of cyanamide.

The solvent employed in this reaction is preferably an inert aprotic, organic solent such as dialkylamides and dialkylsulfoxides which are liquid at the reaction temperature. Examples of such solvents include dimethylformamide, dimethylacetamide, dimethylsulfoxide, diethylformamide, diethylacetamide and the like.

For improved reaction yields of oxazoline and length of time of reaction, a catalytic quantity of base is preferred. Bases which can be employed are carbonates of metals such as potassium, lithium, and sodium; bicarbonates such as potassium, lithium and sodium; and ammonia. Organic bases such as pyridine, lutidine and triethylamine can also be used. The most preferred base is potassium bicarbonate. When using a solid material such as potassium bicarbonate, it is found to be preferable that it is micronized. A dry, free flowing material appears to provide better yields.

The quantity of catalyst employed is from about 10–30 g./150 g. of D-arabinose when using a solid catalyst. If a liquid catalyst is employed, the quantity of catalyst is from about 0.1 to 1.0 mole equivalent of D-arabinose.

The reaction can be conveniently carried out at a temperature of from about 30° to about 130° C. The lower end of the temperature range is somewhat dependent upon the reaction time. Oxazoline will be formed, but at a lower rate. The upper end of the temperature range is dependent upon the yield of oxazoline one desires. For example, as the temperature increases, oxazoline degrades more readily.

The reaction time is dependent upon the temperature. However, it has been found that a reaction time of 75 minutes at a temperature of 90° C. brings about a good yield of oxazoline in a reasonable length of time.

The oxazoline is now converted to the cyclocytidine salt by reaction with the cyanovinylating agent, cis-β-[trimethylammonium]-acrylonitrile tosylate. The oxazoline can be reacted directly with the acrylonitrile without isolation from its reaction vessel, if desired. Otherwise the oxazoline can be isolated by standard techniques of crystallization and then converted to the cyclocytidine salt by the cyanovinylation process.

The cyanovinylation is carried out by reacting the aminooxazoline with cis-β-[trimethylammonium]-acrylonitrile tosylate. To obtain significant yields of the cyclocytidine salt, the reaction should be run in an inert, aprotic solvent such as the dialkylamides, for example, formamides, acetamides and other amides which are liquid at the reaction temperature. Examples of such solvents include dimethylformamide, dimethylacetamide, diethylformamide and the like. The length of time of the reaction is dependent upon the temperature. A temperature range of from about 30° to about 100° C. is generally satisfactory. A temperature range of from about 40° to about 60° C. brings about a good compromise between yield and length of the reaction. It is preferred to carry out this reaction in a flowing nitrogen atmosphere. Under these circumstances, the cyclocytidine salt is recovered as a white crystalline material. If an inert, mobile atmosphere such as nitrogen is not employed, the cyclocytidine salt is recovered as a yellow crystalline material. Analyses indicate these materials are the same. Although the reason for the observed color difference is not clear, it is believed that trimethylamine provides color to the crystals. If nitrogen is passed through the reaction vessel, the trimethylamine is driven off and white crystalline material is isolated.

As in the Orgel and Sanchez patent, previously cited, the cyclocytidine salt is readily converted to cytosine arabinoside by contacting with a dilute base such as sodium hydroxide or aqueous ammonia at room temperature or a slightly elevated temperature, for example, from 25° to about 75° C. This results in an essentially quantative yield of cytosine arabinoside and side product tosic acid. These are readily separated on a strong acid resin such as a macroreticular resin, Dowex MSC-1. The cytosine arabinoside is then further purified in a conventional manner.

The cis-β-[trimethylammonium]-acrylonitrile tosylate is prepared as follows: Isoxazole is selectively converted to the anion of cis-1-cyano-2-hydroxyethylene by contacting in an inert, aprotic solvent isoxazole with a base of strength greater than or equal to that of sodium methoxide at a temperature of less than or equal to about −40° C. As previously stated, the temperature of the isoxazole at the time of addition is critical. For example, if the isoxazole enters the reaction vessel at ambient temperature, the temperature in the vessel should be less than or equal to −40° C. However, if the isoxazole is cooled to −° C. prior to entrance into the reaction vessel, the reaction temperature may be maintained at less than or equal to −20° C. Various combinations of isoxazole precooling and reaction vessel temperature maintenance are available for the selective production of the cis anion.

The inert organic solvents are liquid at the reaction temperature. Examples of inert organic solvents are the ethers of two to eight carbon atoms, inclusive, and cyclic ethers of four to eight carbon atoms, inclusive. Examples of such solvents include diethyl ether, dipropyl ether, dimethylformamide, diethylacetamide and the like. Additional solvents which are appropriate include 1,2-dimethoxyethane and tetrahydrofuran.

Examples of bases of appropriate strength are t-butoxide, t-amyloxide, isopropoxide, methoxide, ethoxide, and the like. Generally the cation is a metal such as sodium, potassium, lithium, etc. A preferred base solvent system is potassium tert-butoxide in tetrahydrofuran.

The temperature may be as low as is consonant with a satisfactory reaction rate. Reaction temperatures significantly above −40° C., assuming essentially no precooling of isoxazole, should be avoided since trans isomer production occurs to an undesirable extent.

The 1-cyano-2-hydroxyethylene anion is converted to a tosylate salt by standard reagents such as reaction with tosyl halide or tosyl anhydride. In order to maintain high yields, the temperature of the reaction should initially be maintained at a level less than or equal to the temperature used for the production of the cis anion. No additional solvent is necessary although a solvent in which the salt of 1-cyano-2-hydroxyethylene is soluble may be added. An example of such a solvent is acetonitrile. The by-products of the reaction are separated by extraction of the cis-β-tosyoxyacryonitrile with an organic solvent such as ethyl acetate, toluene or benzene combined with aqueous base.

After purification, the cis-β-tosyloxyacrylonitrile prepared above is now reacted with trimethylamine in a stereospecific reaction resulting in retention, thereby forming the cis-β-[trimethylammonium]acrylonitrile tosylate. The reaction temperature is generally from about +5° to about 50° C. The reaction can be carried out in the solvent employed in the previous extraction step for separating the by-products from the cis-β-tosyloxyacrylonitrile.

Following are examples illustrating the nature of the invention. They are not intended to narrow the scope of the invention.

EXAMPLE 1

Oxazoline of D-arabinose

A cyanamide solution (110 ml., containing approximately 61 g. cyanamide), 42 g. of $CaCl_2.2H_2O$ and 420 ml. ethyl acetate is shaken and the aqueous phase discarded. The organic phase is backwashed with 40 ml. of 25% aqueous sodium chloride.

The ethyl acetate phase is dried over magnesium sulfate, filtered and concentrated under vacuum to a small volume, 100 ml. isopropanol added and concentrated under vacuum to dryness.

The isopropanol is used to azetrope away any water present at a temperature of ca. 45°. The product cools and solidifies to a white solid, wt. 40.97 g. After drying on high vacuum for 1 hour, the weight has not decreased (40.87 g.). This corresponds to approximately 67% of the cyanamide from one extraction with ethyl acetate at a volume ratio of 2.5:1 ethyl acetate/aqueous phease.

A mixture of (90.0 g., 600 mmole) D-arabinose, cyanamide (31.0 g., 740 mmole, 1.23 eq) and mortared potassium bicarbonate (3.60 g., 36 mmole 0.06 eq) is stirred at 90° in 600 ml. dimethylformamide. After ca. 5 minutes, the mixture is a pale yellow solution and after another 6 minutes, the solution deposits crystals of product. It is stirred 75 minutes at 90° C. after the product precipitates, then cooled to 30°. Ethyl acetate (360 ml.) is added over ca. 15 minutes, the suspension stirred 30 minutes at 25° C. and stirred 1 hour at 0° C. The crystals are filtered and washed with 2 × 100 ml. of 1:1 ethyl acetate dimethylformamide, washed with 150 ml. ethyl acetate and dried at 60° C. at 27 inch Hg overnight to give 88.1 g. (85%) of off-white crystalline oxazoline mp 173.5°–174.5°.

EXAMPLE 2

Cis-β-[triethylammonium]-acrylonitrile tosylate

Into a 1.0 l. jacketed, 3-neck flask is added a solution of potassium t-butoxide in tetrahydrofuran (273 g., 55.4 g., KOtBu, 495 mmole). This material is assayed at 20.3% KOtBu, 0.40% KOH, 0.9103 g/ml.). The solution is cooled to −45° and then a solution of isoxazole, (27.60 g., 400 mmole) in dry tetrahydrofuran (50 ml.) is added dropwise at such a rate that temperature is maintained at −39° or lower (the addition takes 31 minutes). After approximately 5 minutes of addition, a white precipitate of the salt develops and by the end of the addition the mixture is a thick slurry. The slurry is stirred 30 minutes further at −40° to −45°. Solid tosyl chloride (92.5 g., 486 mmole) is added in portions at such a rate that the temperature stays below −38° and the white suspension turns black. The addition takes about 13 minutes.

Acetonitrile (300 ml.) is added dropwise over 6 minutes and the temperature stays at −43° C. After stirring overnight at −10°, the mixture is concentrated to a small volume (wt. 131 g.), 750 ml. toluene added and the mixture extracted with 2 × 500 ml. 5% Na$_2$CO$_3$ portions. This is back extracted with 100 ml. toluene. The backwash gives an emulsion and is filtered to remove a black solid. The toluene extracts are combined, dried over sodium sulfate, and stirred with 10 g. Darco G60 for thirty minutes. This is filtered and washed well to give a pale brown solution of cis-β-tosyloxyacrylonitrile. The isomer ratio is 95.5% cis and 4.5% trans.

The toluene solution is concentrated to 1000 g. wt., and stirred at 35°–40° C. A solution of trimethylamine (50 ml., 32.8 g., 560 mmole) in 150 ml. cold toluene is added dropwise over ca. 30 minutes. During this addition, crystals of cis-quaternary salt precipitate. The crystal slurry is stirred 2 hours at room temperature, filtered, and washed with 75 ml. toluene, followed by 75 ml. of 2:1 toluene:methylene chloride. The slurry is further washed with two 75 ml. portions of pentane and dried to give 106.1 g. of pale brown solid (94%).

EXAMPLE 3

Cyclocytidine Salt

A mixture of oxazoline (13.051 g., 75 mmole), the cis-quaternary salt of Example 2, and 75 ml. of dimethylformamide is stirred at 50° for 10.5 hours with a nitrogen sparge of 1 ft.$^3$/min and through a dimethylformamide bubbler at room temperature to presaturate the nitrogen with dimethylformamide.

Acetonitrile (300 ml.) is added rapidly and the solution seeded to develop crystals of the cyclocytidine salt. The slurry is slowly cooled to room temperature over 30 minutes, then to 0° over ca. 1 hour, and stirred another 1 hour at 0°. The crystals are filtered, and washed with two 20 ml. portions of acrylonitrile:methylformide followed by two 25 ml. portions of acrylonitrile and dried at 60° at 27" Hg overnight to give 23.30 g. (71%) of white solid.

EXAMPLE 4

Cytosine Arabinoside

Cyclocytidine salt (8.0023 g., 18.25 mmole) and 80 ml. of 2N ammonium hydroxide are stirred at 58°. Hydrolysis is complete at 70 minutes.

The cytosine arabinoside is isolated by ion exchange chromatography.

I claim:
1. Cis-β-[trimethylammonium]-acrylonitrile tosylate.

* * * * *